United States Patent [19]

Rice

[11] Patent Number: 5,431,623
[45] Date of Patent: Jul. 11, 1995

[54] KNEE HYPERTENSION BLOCK ORTHOSIS

[75] Inventor: Jon F. Rice, Omaha, Nebr.

[73] Assignee: Board of Regents Univ. of Nebraska, Lincoln, Nebr.

[21] Appl. No.: 150,366

[22] Filed: Nov. 9, 1993

[51] Int. Cl.⁶ .......................... A61F 5/04; A41D 13/00
[52] U.S. Cl. ............................... 602/26; 2/22; 2/2; 602/23
[58] Field of Search ............ 602/23, 26, 5, 25, 3; 2/2, 22, 23, 24

[56] References Cited

U.S. PATENT DOCUMENTS

| | | | |
|---|---|---|---|
| 4,139,002 | 2/1979 | Almedia | 602/26 X |
| 4,349,016 | 9/1982 | Glassman et al. | 602/23 |
| 4,387,709 | 6/1983 | Shen | 602/26 |
| 4,409,689 | 10/1983 | Buring et al. | 2/22 |
| 4,633,529 | 1/1987 | Litz | 2/22 |
| 4,781,179 | 11/1988 | Colbert | 602/26 X |
| 4,884,561 | 12/1989 | Letson, Sr. | 2/24 X |
| 5,063,916 | 11/1991 | France et al. | 602/26 |
| 5,107,823 | 4/1992 | Fratesi | 2/22 X |

Primary Examiner—Richard J. Apley
Assistant Examiner—Beverly A. Meindl
Attorney, Agent, or Firm—Zarley, McKee, Thomte Voorhees & Sease; Mark D. Frederiksen

[57] ABSTRACT

A knee hyperextension orthotic device includes an elongated plate which is curved to form a flush fit against a patient's leg, with an upper portion fastened anterior of the thigh, a lower portion fastened anterior of the lower leg and a central portion fastened anterior of the knee. The central portion of the plate has a narrower width than the upper and lower portions, forming rearwardly extending wings on the upper and lower plate portions. A pair of length adjustable straps are connected between the upper and lower wings on each side of the plate, to permit adjustment of the angle of maximum knee extension. A central strap is connected to the central plate portion and extends posterior of the knee to maintain the knee in appropriate position within the orthotic device. A plurality of apertures in the plate permit the leg to "breathe" when the device is being worn.

11 Claims, 2 Drawing Sheets

KNEE HYPERTENSION BLOCK ORTHOSIS

TECHNICAL FIELD

The present invention relates generally to splints and bracing for knee hyperextension, and more particularly to an improved knee hyperextension block orthosis for controlling primary genu recurvatum.

BACKGROUND OF THE INVENTION

Genu recurvatum is a commonly observed postural deformity in children with cerebral palsy or developmental delay. Genu recurvatum is a consequence of a poor control over the knee joint due to muscle weakness, generalized weakness of the lower extremities, or ligamentous or capsular laxity at the knee.

The prior art has treated genu recurvatum with surgical intervention, bracing intervention, or both. Bracing intervention has included long leg braces with attached ankle-foot orthosis (AFO) or double uprights connected to the shoe, various types of AFOs, a Swedish knee cage, or a knee hyperextension control splint. However, these methods for controlling hyperextension of the knee often fail, or are cumbersome to use.

SUMMARY OF THE INVENTION

It is therefore a general object of the present invention to provide an improved knee hyperextension block orthosis (KHBO).

Another object of the present invention is to provide a KHBO which allows free knee flexion during swing and during floor activities.

Another object is to provide a KHBO which limits knee hyperextension on stance.

Still another object of the present invention is to provide a KHBO which is light weight, aesthetically pleasing, and easy to use with various types of clothing.

These and other objects will be apparent to those skilled in the art.

The knee hyperextension orthotic device of the present invention includes an elongated plate which is curved to form a flush fit against a patient's leg, with an upper portion fastened anterior of the thigh, a lower portion fastened anterior of the lower leg and a central portion fastened anterior of the knee. The central portion of the plate has a narrower width than the upper and lower portions, forming rearwardly extending wings on the upper and lower plate portions. A pair of length adjustable straps are connected between the upper and lower wings on each side of the plate, to permit adjustment of the angle of maximum knee extension. A central strap is connected to the central plate portion and extends posterior of the knee to maintain the knee in appropriate position within the orthotic device. A plurality of apertures in the plate permit the leg to "breathe" when the device is being worn.

DESCRIPTION OF THE PREFERRED EMBODIMENT

Figure 1:
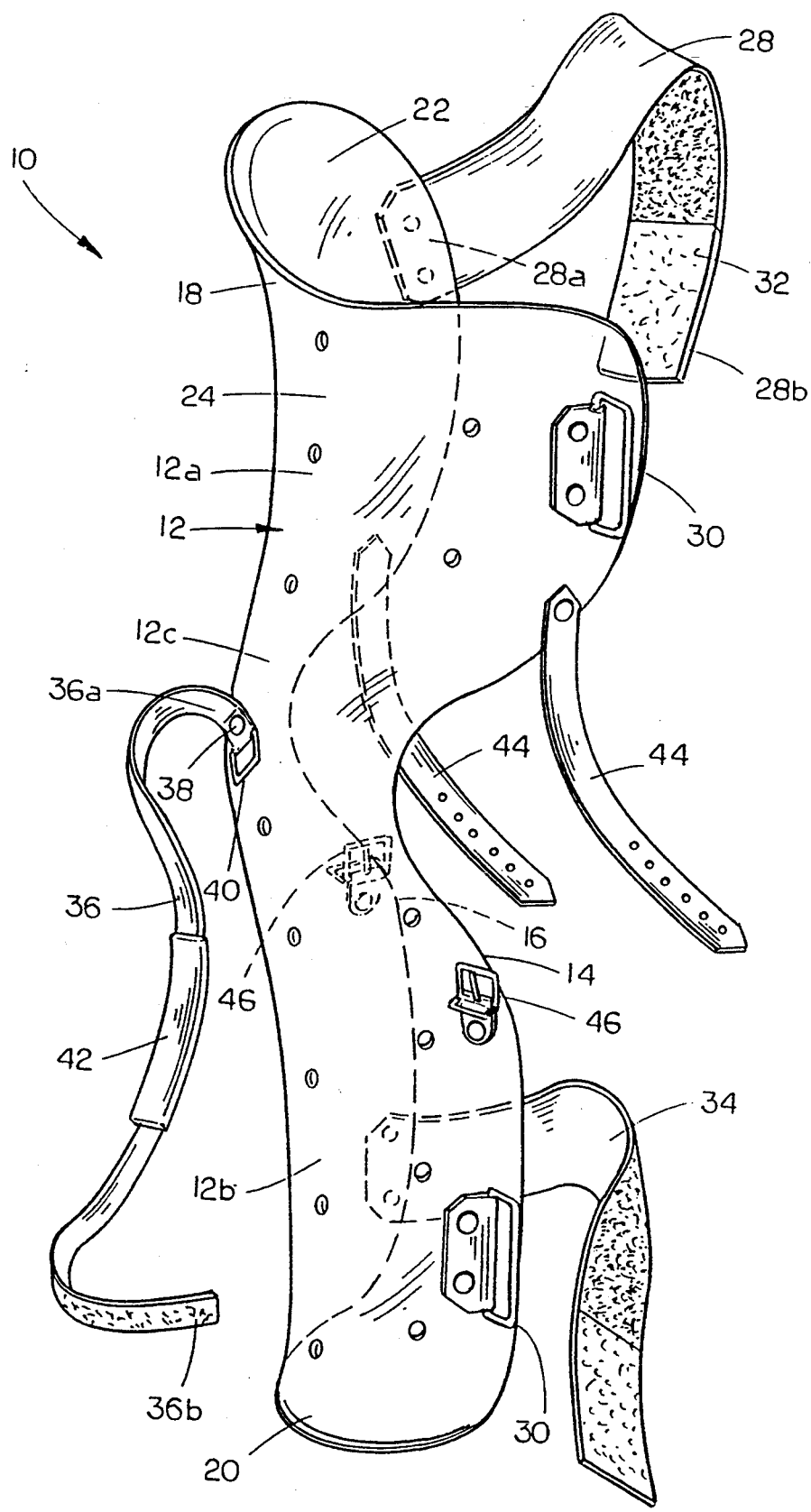
FIG. 1 is a perspective view of the knee hyperextension block orthosis of the present invention.

Referring now to the drawings, in which similar or corresponding parts are identified with the same reference numeral, and more particularly to FIG. 1, the knee hyperextension block orthosis (KHBO) of the present invention is designated generally at 10 and includes a plate 12 of a resilient, light-weight, thin sheet of plastic material having longitudinal and opposing side edges 14 and 16, upper and lower edges 18 and 20, and interior and exterior surfaces 22 and 24 respectively.

Figure 2:
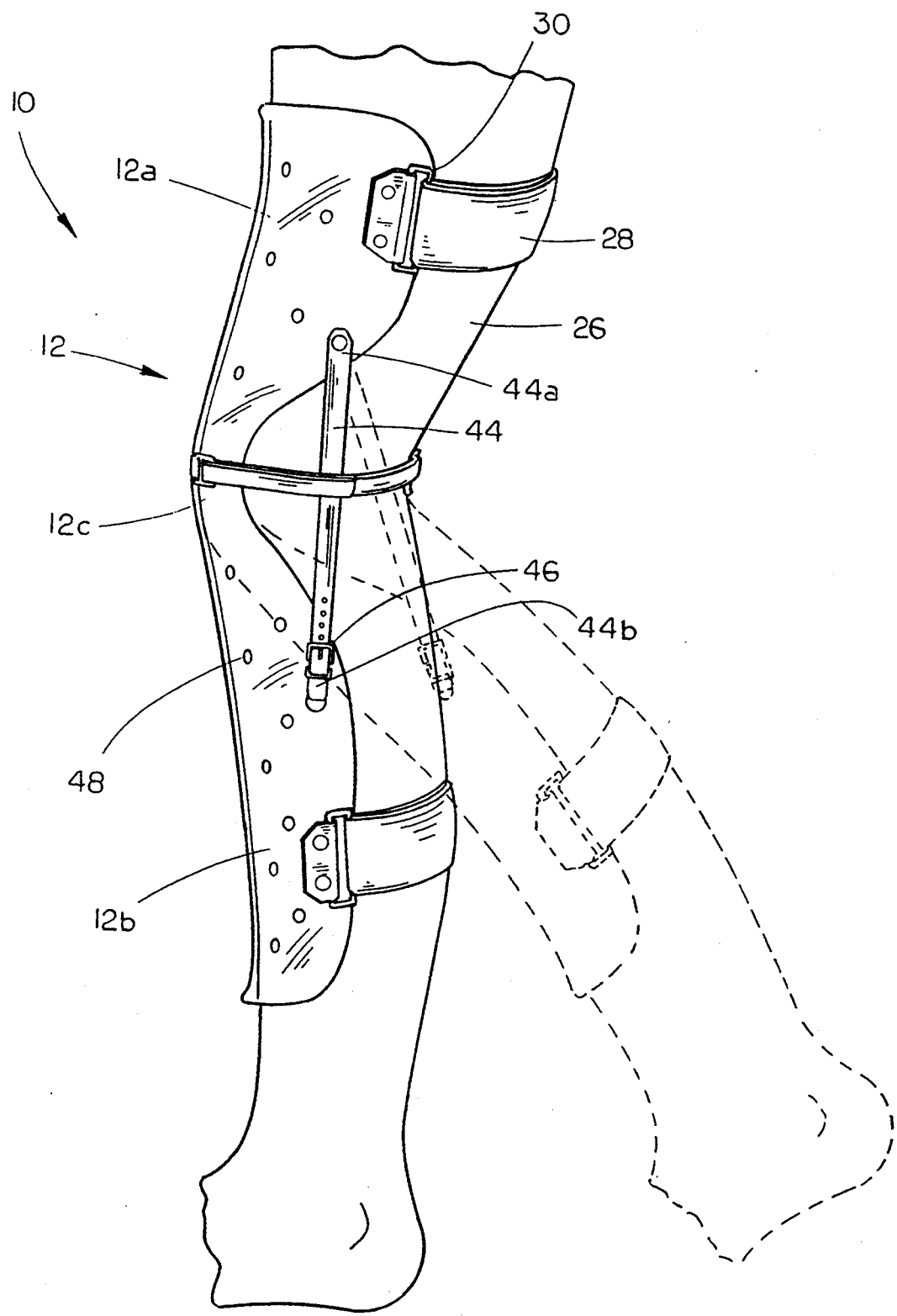
FIG. 2 is a side elevational view of the orthosis of the present invention applied to a patient's knee.

As shown in FIGS. 1 and 2, plate 12 is curved transversely to its longitudinal axis to follow the curvature of the anterior surface of the user's leg 26. As shown in FIG. 2, plates 12 includes an upper portion 12a fitted to the anterior portion of the thigh, a lower portion 12b fitted to the anterior portion of the lower leg and a central portion 12c connecting upper and lower portions 12a and 12b and located on the anterior of the knee over the patella. Upper and lower portions 12a and 12b have a transverse width greater than that of central portion 12c, such that central portion 12c is relatively flat and more flexible to permit knee flexion.

As shown in FIG. 1, an elongated strap 28 has one end 28a fastened to upper portion 12a adjacent side edge 16. Strap 28 extends around the posterior of the femur (as shown in FIG. 2) and is threaded through a ring 30 fastened to upper portion 12a adjacent the opposing edge 14. Strap 28 includes hook and loop fastener material 32 on the free end 28b such that the free end may be threaded through ring 30 and removably and adjustably fastened back upon itself.

A second strap 34 is fastened in a similar fashion to lower portion 12b and threaded through a second ring 30 so as to adjustably fasten lower portion 12b to leg 26. A central strap 36 has one end fastened to the front surface 24 of central portion 12c, as shown in FIG. 1. Strap 36 may be fastened with a rivet 38 or other fastener so as to be pivotable. The fastened end 36a has a ring 40 connected thereto which will receive the free end 36b of strap 36. Hook and loop fastener material is also mounted on the free end 36b of strap 36 to permit adjustable and selective fastening. A pad 42 is centrally mounted on strap 36, and located so as to be positioned on the posterior of the knee of the leg.

Although there is some inherent resistance to knee flexion, because of the plastic material utilized in forming plate 12, the design of KHBO allows free knee flexion. Knee hyperextension is limited by a pair of webbing bands 44 on the lateral sides of the knee joint, which are adjustable in length in order to limit knee extension to −5° to −15°. While the bands 44 may be adjusted to permit greater angles, most users would utilize an angle between −5° to −15°. As shown in FIG. 2, the upper end 44a of band 44 is pivotally connected to upper portion 12a and extends downwardly therefrom with free end 44b looped through a buckle for selective length adjustment. Buckle 46 is pivotally attached to lower portion 12b, as shown in FIG. 1. A similar band 44 and buckle 46 are also attached along the opposing longitudinal edge 16, diametric to band 44 and buckle 46 along edge 14.

As shown in FIG. 2, plate 12 may be set in a predetermined amount of knee flexion by adjustment of straps 44 in buckles 46. Because straps 44 extend from upper portion 12a to lower portion 12b at locations posterior of the longitudinal side edges of central portion 12c, shortening the length of straps of 44 will increase the amount of knee flexion, while lengthening straps 44 will decrease the amount of knee flexion.

Continuing to refer to FIG. 2, the orthotic device 10 of the present invention is designed to be flush fitting against the leg, and formed of a thin plastic material. This allows the device to be easily worn under the patient's clothing, and at times is not even visible. In order to prevent perspiration under the device 10, a plurality of apertures 48 are provided across the entire extent of plate 12, to permit "breathing". In addition, a cotton stockinette can be worn under the device 10 to permit breathing.

Whereas the invention has been shown and described in connection with the preferred embodiment thereof, it will be understood that many modifications, substitutions and additions may be made which are within the intended broad scope of the appended claims. There has therefore been shown and described an improved orthotic device which is light weight, aesthetically appealing, which allows free knee flexion during swing and during floor activities, limits knee extension during swing, and which limits knee hyperextension on stance.

I claim:

1. An orthotic device for the prevention of hyperextension of a knee on a patient's leg, comprising:
   an elongated plate of resilient material, having upper and lower edges and longitudinal side edges;
   said plate including an upper portion for attachment to the patient's leg above the knee, a lower portion for attachment to the patient's leg below the knee and a central portion connecting the upper and lower portions for attachment anterior of the patient's knee;
   said upper, central and lower portions being integral areas of a single resilient plate;
   first means for removably attaching the upper plate portion to the leg;
   second means for removably attaching the lower plate portion to the leg;
   said plate formed of a material with memory so as to resist flexion; and
   length adjustable means for connecting the upper plate portion to the lower plate portion to retain the plate flexed against the biasing of the memory of the material, at a predetermined angle of flexion.

2. The orthotic device of claim 1, wherein said plate is curved rearwardly from its longitudinal axis to its longitudinal sides, said upper portion curved for a flush fit against an anterior side of the patient's thigh, said lower portion curved for a flush fit against an anterior side of the patient's lower leg.

3. The orthotic device of claim 2, wherein said upper and lower portions have a greater transverse width from side edge to side edge than the central plate portion, forming wing portions on said upper and lower portions which project rearwardly relative to the side edges of the central plate portion.

4. The orthotic device of claim 3, wherein said length adjustable means include a first end connected to one wing portion of the upper plate portion and an opposing second end connected to one wing portion of the lower plate portion.

5. The orthotic device of claim 3, wherein said length adjustable means includes a first strap extending generally vertically between wing portions of said upper and lower plate portion along one longitudinal side edge, and a second strap extending generally vertically between wing portions of said upper and lower plate portions along the opposing second longitudinal side edge.

6. An orthotic device for the prevention of hyperextension of a knee on a patient's leg, comprising:
   an elongated plate of resilient material, having upper and lower edges and longitudinal side edges;
   said plate including an upper portion for attachment to the patient's leg above the knee, a lower portion for attachment to the patient's leg below the knee and a central portion connecting the upper and lower portions for attachment anterior of the patient's knee;
   said plate being curved rearwardly from its longitudinal axis to its longitudinal sides, said upper portion curved for a flush fit against an anterior side of the patient's thigh, and said lower portion curved for a flush fit against an anterior side of the patient's lower leg;
   said upper and lower portions having a greater transverse width from side edge to side edge than the central plate portion, forming wing portions on said upper and lower portions which project rearwardly relative to the side edges of the central plate portion;
   first means for removably attaching the upper plate portion to the leg;
   second means for removably attaching the lower plate portion to the leg; and
   length adjustable means for connecting the upper plate portion to the lower plate portion to retain the central plate portion flexed at a predetermined angle of flexion; and
   said length adjustable means including a first end connected to one wing portion of the upper plate portion and an opposing second end connected to one wing portion of the lower plate portion.

7. The orthotic device of claim 6, further comprising means for removably attaching said central plate portion to the anterior of the patient's knee.

8. The orthotic device of claim 6, wherein said plate includes a plurality of perforations therethrough to permit the passage of air through the plate when the device is attached to a patient's leg.

9. The orthotic device of claim 6, wherein said length adjustable means are located rearwardly of the side edges of said central plate portion.

10. An orthotic device for the prevention of hyperextension of a knee on a patient's leg, comprising:
    an elongated plate of resilient material, having upper and lower edges and longitudinal side edges;
    said plate including an upper portion for attachment to the patient's leg above the knee, a lower portion for attachment to the patient's leg below the knee and a central portion connecting the upper and lower portions for attachment anterior of the patient's knee;
    said plate being curved rearwardly from its longitudinal axis to its longitudinal sides, said upper portion curved for a flush fit against an anterior side of the patient's thigh, and said lower portion curved for a flush fit against an anterior side of the patient's lower leg;
    said upper and lower portions having a greater transverse width from side edge to side edge than the central plate portion, forming wing portions on said upper and lower portions which project rearwardly relative to the side edges of the central plate portion;
    first means for removably attaching the upper plate portion to the leg;
    second means for removably attaching the lower plate portion to the leg; and length adjustable means for connecting the upper plate portion to the lower plate portion to retain the central plate portion flexed at a predetermined angle of flexion; and said length adjustable means including a first strap extending generally vertically between wing portions of said upper and lower plate portion along one longitudinal side edge, and a second strap extending generally vertically between wing portions of said upper and lower plate portions along the opposing second longitudinal side edge.

11. The orthotic device of claim 5, wherein said first strap includes an upper end pivotally connected to said wing portion, and a lower end selectively and adjustably connected to a strap retention means pivotally mounted on said lower plate wing portion, and wherein said second strap includes a first end pivotally connected to said upper plate wing portion and a lower end removably and adjustably connected to a strap retention means pivotally mounted on said lower plate wing portion.

* * * * *